(12) United States Patent
Yang

(10) Patent No.: US 9,702,797 B2
(45) Date of Patent: Jul. 11, 2017

(54) SUPPORTING APPARATUS AND TORSION TEST MEASURING DEVICE USING SAME

(71) Applicant: ScienBiziP Consulting (Shenzhen) Co., Ltd, Shenzhen (CN)

(72) Inventor: Guang Yang, Shenzhen (CN)

(73) Assignee: ScienBiziP Consulting(Shenzhen)Co., Ltd., Shenzhen (CN)

( * ) Notice: Subject to any disclaimer, the term of this patent is extended or adjusted under 35 U.S.C. 154(b) by 104 days.

(21) Appl. No.: 14/694,820

(22) Filed: Apr. 23, 2015

(65) Prior Publication Data

US 2016/0061702 A1 Mar. 3, 2016

(30) Foreign Application Priority Data

Sep. 1, 2014 (CN) .......................... 2014 1 0439714

(51) Int. Cl.
| | |
|---|---|
| G01L 3/00 | (2006.01) |
| G01N 3/22 | (2006.01) |
| B25H 1/00 | (2006.01) |
| F16M 11/18 | (2006.01) |
| F16M 11/04 | (2006.01) |
| G01L 5/00 | (2006.01) |
| G01L 25/00 | (2006.01) |
| G01D 11/30 | (2006.01) |
| G01L 5/24 | (2006.01) |
| B25B 23/00 | (2006.01) |
| B25B 21/00 | (2006.01) |

(52) U.S. Cl.
CPC .............. *G01N 3/22* (2013.01); *B25H 1/005* (2013.01); *B25B 21/00* (2013.01); *B25B 23/00* (2013.01); *F16M 11/046* (2013.01); *F16M 11/18* (2013.01); *F16M 2200/047* (2013.01); *G01D 11/30* (2013.01); *G01L 5/0042* (2013.01); *G01L 5/24* (2013.01); *G01L 25/003* (2013.01); *G01N 2203/0021* (2013.01)

(58) Field of Classification Search
CPC ................ G01L 25/003; G01L 5/0042; G01N 2203/0021; G01N 3/22; G01D 11/30; F16M 11/18; F16M 11/046; F16M 2200/047; B25B 23/00; B25B 21/00; B25H 1/005
USPC ........................................ 324/750.22, 756.01
See application file for complete search history.

(56) References Cited

U.S. PATENT DOCUMENTS

| | | | | |
|---|---|---|---|---|
| 5,181,425 A | * | 1/1993 | Livingston ............ | G01L 25/003 73/1.11 |
| 5,353,654 A | * | 10/1994 | Lin ........................ | G01M 99/00 73/808 |

(Continued)

*Primary Examiner* — Jonathan Dunlap
(74) *Attorney, Agent, or Firm* — Steven Reiss

(57) ABSTRACT

A supporting apparatus includes a supporting assembly including a fixed member, a mounting member fixed to the fixed member and a lifting assembly. The mounting member includes a mounting portion having a first side, a second side opposite and parallel to the first side, and a top side coupling the first side with the second side. The lifting assembly includes a support member slidably attached to the first side of the mounting portion, a lifting member slidably attached to the second side of the mounting portion, at least one fixed pulley attached to the top side of the mounting portion, a connecting member arranged on the at least one fixed pulley, and coupling the support member with the lifting member, and one or more weight elements attachable to the lifting member.

14 Claims, 4 Drawing Sheets

(56) References Cited

U.S. PATENT DOCUMENTS

| | | | | |
|---|---|---|---|---|
| 5,597,964 A * | 1/1997 | Binns | | G01L 5/0042 73/761 |
| 5,703,277 A * | 12/1997 | Grabovac | | G01L 25/003 73/1.09 |
| 5,886,246 A * | 3/1999 | Bareggi | | G01L 25/003 73/1.09 |
| 6,133,726 A * | 10/2000 | Heigl | | G01R 31/2887 324/756.01 |
| 6,646,431 B1 * | 11/2003 | Parvez | | G01R 1/06705 324/750.22 |
| 6,715,362 B2 * | 4/2004 | Chiapuzzi | | G01L 25/003 73/1.09 |
| 6,718,831 B2 * | 4/2004 | Chiapuzzi | | G01L 25/003 73/1.09 |
| 6,772,645 B2 * | 8/2004 | Hsien | | G01L 3/06 73/862.191 |
| 7,252,013 B2 * | 8/2007 | Hammond, Jr. | | G01N 3/22 73/856 |
| 8,453,519 B2 * | 6/2013 | Zhang | | G01L 5/0042 73/862.08 |
| D696,149 S * | 12/2013 | McCracken | | D10/103 |
| 8,650,928 B2 * | 2/2014 | Herbold | | G01L 25/003 73/1.12 |
| 9,046,433 B2 * | 6/2015 | Hsieh | | F16B 31/02 |
| 9,250,170 B2 * | 2/2016 | Su | | G01N 3/22 |
| 2004/0093959 A1 * | 5/2004 | Hsien | | G01L 3/06 73/862.191 |
| 2007/0068277 A1 * | 3/2007 | Hammond | | G01N 3/22 73/856 |
| 2008/0223151 A1 * | 9/2008 | Lai | | G01M 13/04 73/862.08 |
| 2012/0266693 A1 * | 10/2012 | Zhang | | G01L 5/0042 73/862.08 |
| 2014/0202269 A1 * | 7/2014 | Weissacher | | G01D 11/30 73/866.5 |

* cited by examiner

SUPPORTING APPARATUS AND TORSION TEST MEASURING DEVICE USING SAME

FIELD

The subject matter herein generally relates to supporting apparatuses, and especially to a supporting apparatus for supporting and clamping an electric screwdriver and a torsion test measuring device using same.

BACKGROUND

The screws for assembling a thin product are always relatively small, so the torsion of the electric screwdriver for tightening the screws is also relatively small, otherwise, the excessive torsion will damage the screws. To ensure the precise setting for the torsion of the electric screwdriver, the current testing methods are hand holding of an electric screwdriver, and testing the torsion of the electric screwdriver directly on a torsion test measuring device. However, it is difficult to control the power applied to the electric screwdriver, which results in the power applied to the electric screwdriver not always being uniform.

BRIEF DESCRIPTION OF THE DRAWINGS

Many aspects of the present disclosure are better understood with reference to the follow drawings. The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION

Figure 1:
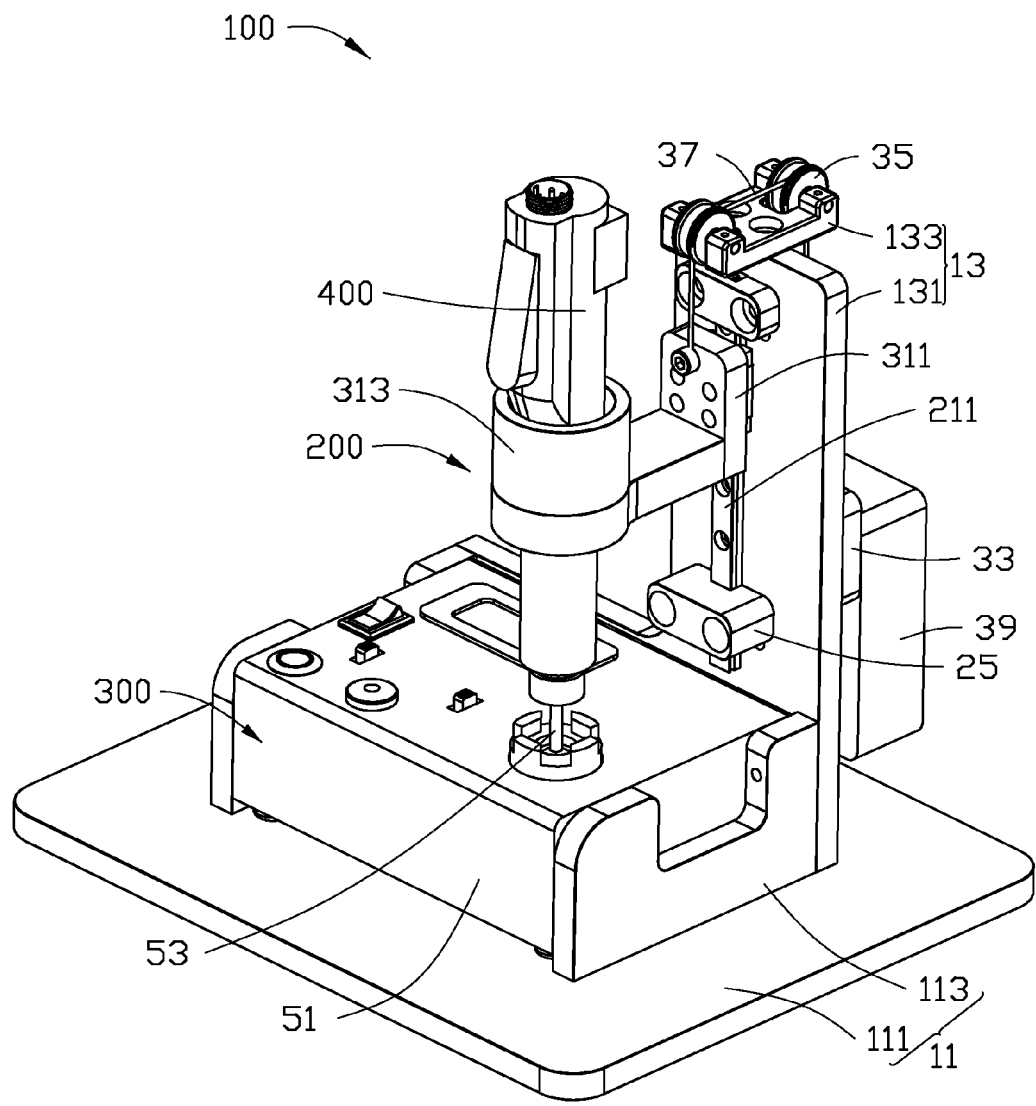
FIG. 1 is an isometric view of an embodiment of a torsion test measuring device from a first angle.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. Also, the description is not to be considered as limiting the scope of the embodiments described herein. The drawings are not necessarily to scale and the proportions of certain parts have been exaggerated to better illustrate details and features of the present disclosure.

The connection can be such that the objects are permanently connected or releasably connected. The term "comprising" when utilized, means "including, but not necessarily limited to"; it specifically indicates open-ended inclusion or membership in the so-described combination, group, series and the like.

FIG. 1 shows a torsion test measuring device 100. The torsion test measuring device 100 can include a supporting apparatus 200, a torsion measuring apparatus 300 and an electric screwdriver 400. The supporting apparatus 200 can be used to support the electric screwdriver 400. The torsion measuring apparatus 300 can be located on the supporting apparatus 200 and used to measure the torsion value of the electric screwdriver 400.

Figure 2:
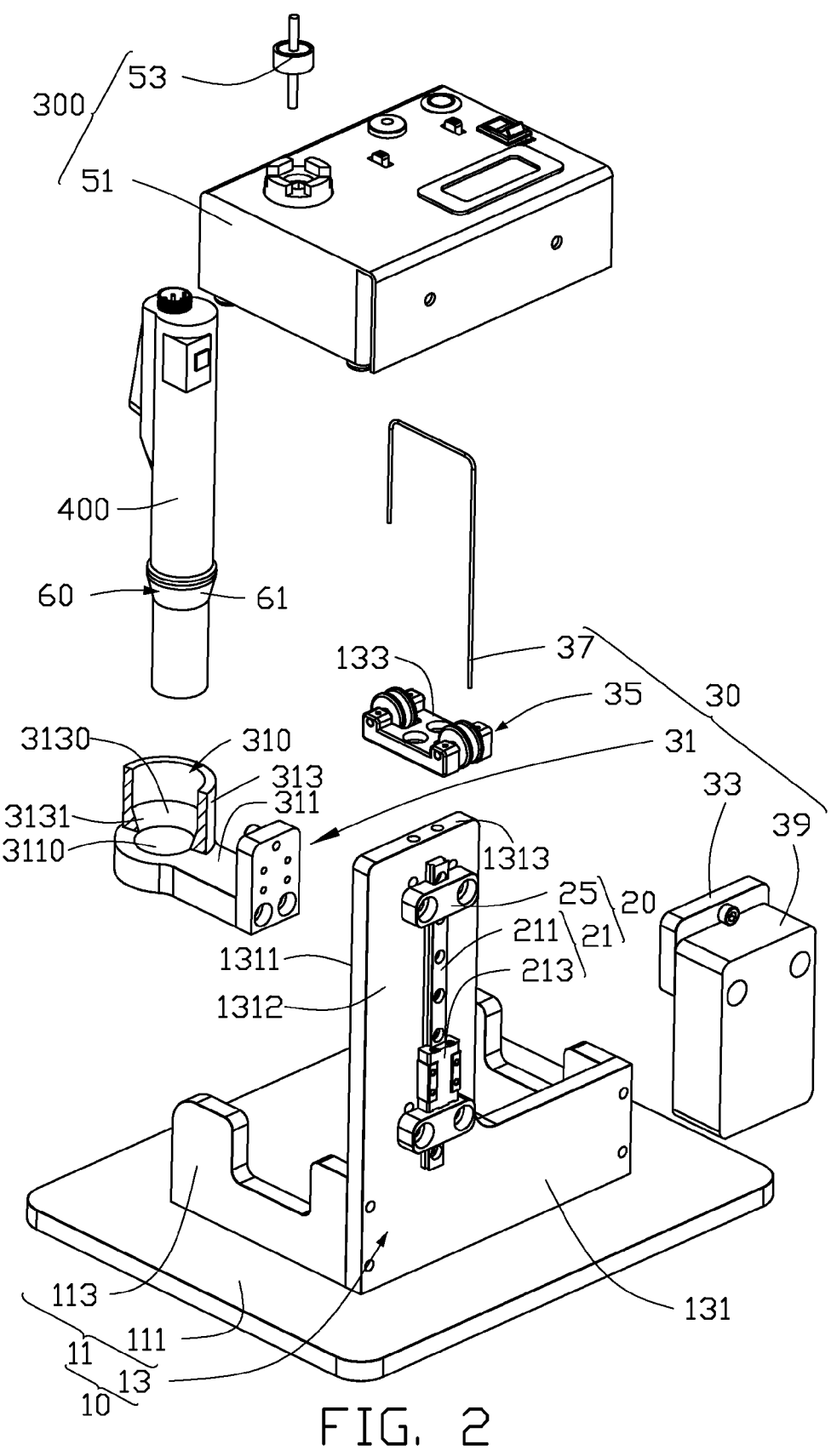
FIG. 2 is an exploded, isometric view of an embodiment of the torsion test measuring device from a second angle.

Referring to FIGS. 1 and 2, the supporting apparatus 200 can include a supporting assembly 10, a sliding assembly 20 and a lifting assembly 30. The sliding assembly 20 can be attached to the supporting assembly 10. The lifting assembly 30 can be attached to the sliding assembly 20. The supporting assembly 10 can include a fixed member 11 and a mounting member 13 fixed to the fixed member 11. The fixed member 11 can include a base plate 111 and two fixed plates 113 fixed to the base plate 111. The base plate 111 can be substantially rectangular shaped. The two fixed plates 113 can be parallel to each other and further perpendicular to the base plate 111 respectively. The mounting member 13 can be fixed to the base plate 111. The mounting member 13 can include a supporting portion 131 and a mounting portion 133. The supporting portion 131 can be L-shaped. The supporting portion 131 can include a first side 1311 close to the two fixed plates 113, a second side 1312 away from the two fixed plates 113 and opposite and parallel to the first side 1311, and a top side 1313 coupling the first side 1311 with the second side 1312. The supporting portion 131 can be fixed to the base plate 111 and further perpendicular to the base plate 111. The supporting portion 131 can be fixed to the two fixed plates 113 and further perpendicular to the two fixed plates 113. The mounting portion 133 can be fixed to one end of the supporting portion 131 distal from the base plate 111, and the two ends of the mounting portion 133 can be located on the first side 1331 and the second side 1332 of the supporting portion 131 respectively.

The sliding assembly 20 can be attached to the supporting portion 131. The sliding portion 20 can include two sliding members 21 and four resisting members 25. Each sliding member 21 can include a sliding rail 211 and a sliding block 213 slidably attached to the sliding rail 211. One sliding rail 211 can be fixed to the first side 1311 of the supporting portion 131, and the sliding rail 211 can be substantially perpendicular to the base plate 111, and the other sliding rail 211 can be fixed to the second side 1312 of the supporting portion 131 away from the fixed plate, and the other sliding rail 211 can be substantially perpendicular to the base plate 111. The two of the four resisting members 25 can be located on two ends of the one sliding rail 211 and further fixed to first side 1311 of the supporting portion 131, and the other two of the four resisting members 25 can be located on two ends of the other sliding rail 211 and further fixed to the second side 1312 of the supporting portion, so as to avoid the sliding block 213 sliding off the sliding rail 211 corresponding to the sliding block 213.

Figure 3:
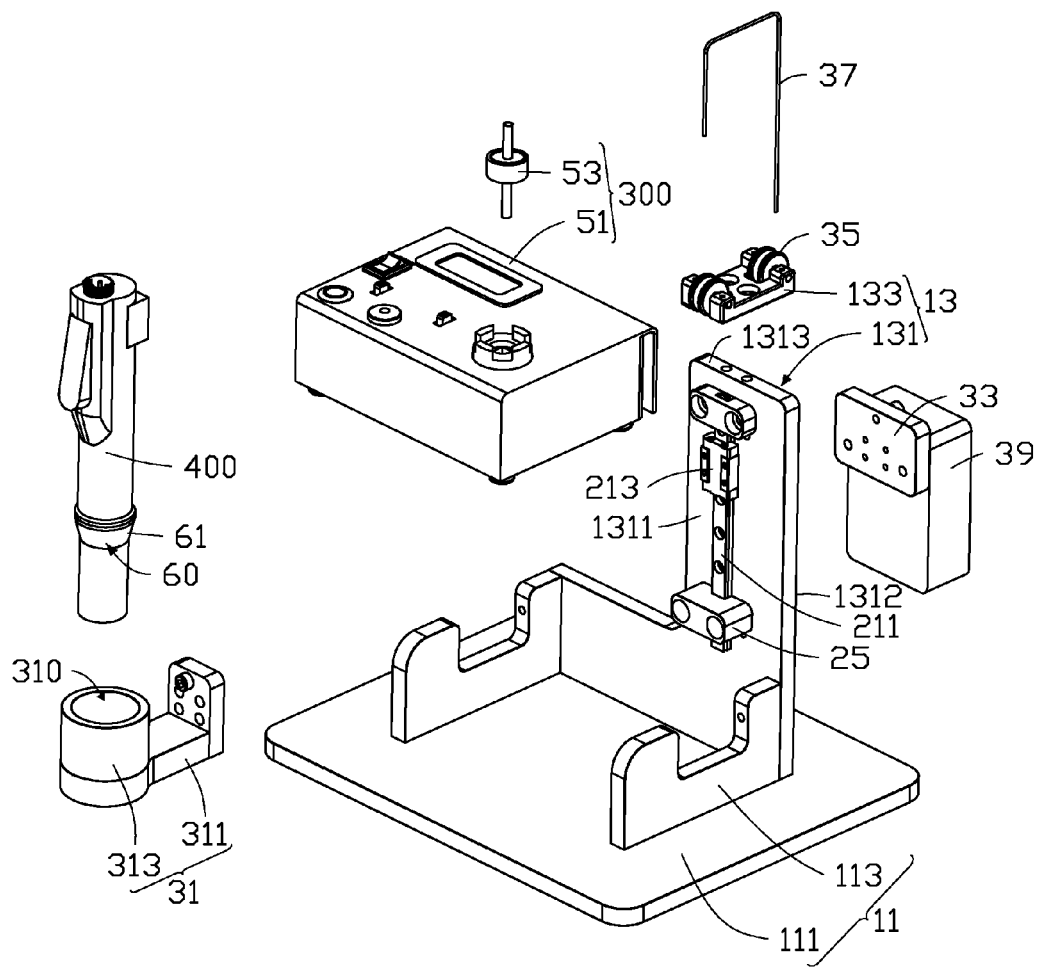
FIG. 3 is an exploded, isometric view of an embodiment of the torsion test measuring device from the first angle.
Figure 4:
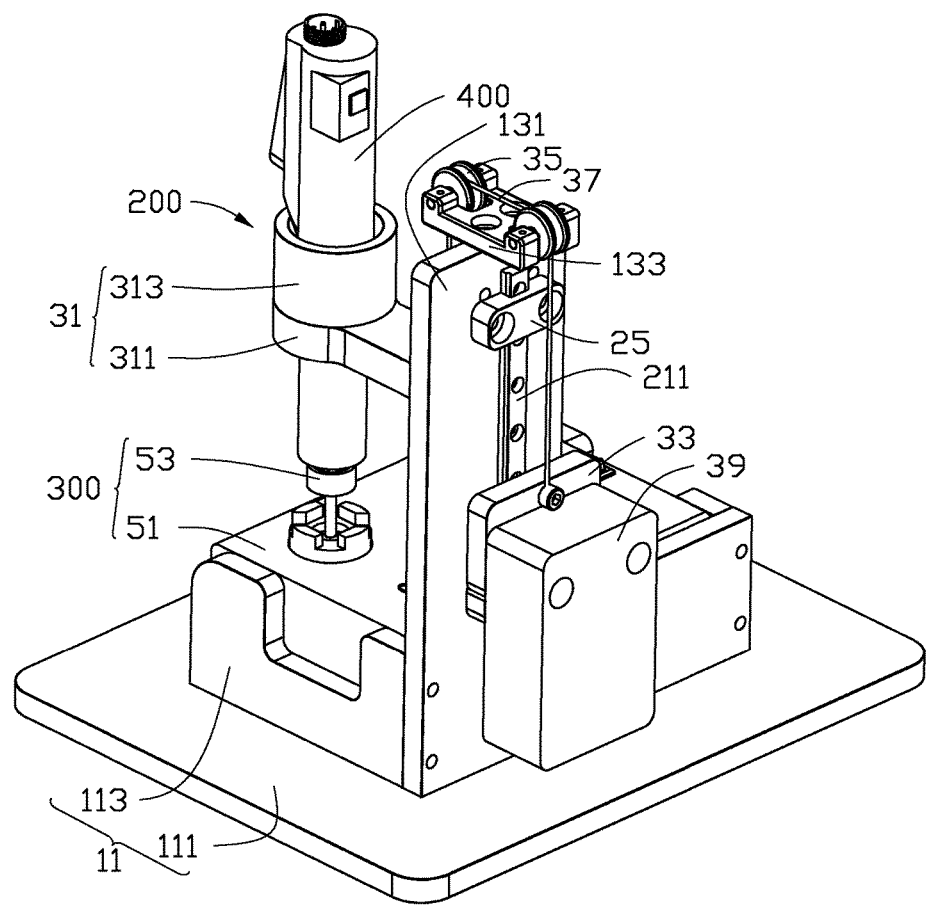
FIG. 4 is an isometric view of an embodiment of a torsion test measuring device from the second angle.

The lifting assembly 30 can include a support member 31, a lifting member 33, two fixed pulleys 35, a connecting member 37 and a number of weight elements 39. The support member 31 can be fixed to the sliding block 213 attacked to the sliding member 21 fixed to the first side 1311 of the supporting portion 131. Referring to FIGS. 2-4, one end of the support member 31 away from the sliding block 213 can define a first through hole 310. In detail, the support member 31 can include a fixed portion 311 and a holding portion 313 fixed to the fixed portion 311. The fixed portion 311 can be L-shaped. One end of the fixed portion 311 close to the supporting portion 131 can be fixed to the sliding block 213 attached to the sliding member 21 fixed to first side 1311 of the supporting portion 131, and the other end of the fixed portion 311 away from the supporting portion 131 can define a second through hole 3110. The holding portion 313 can be hollow-circular-cylinder-shaped. One end of the holding portion 313 can be fixed to the other end of the fixed portion 311, and the central axis of the holding portion 313 can be aligned with the central axis of the second through hole 3110. One end of the holding portion 313 close to the fixed portion 311 can define a taper hole 3130. The diameter of the taper hole 3130 close to the fixed portion 311 can be less than a diameter of the taper hole 3130 away from the fixed portion 311. The holding portion 313 can include a first resisting surface 3131, and the taper hole 3130 can be formed by the first resisting surface 3131. In this embodiment, the second through hole 3110 and the taper hole 3130 can be both parts of the first through hole 310, and the central axis of the second through hole 3110, the taper hole 3130 and the first through hole 310 can be both aligned with each other.

Referring to FIGS. 2 and 3, the lifting member 33 can be plate. The lifting member 33 can be fixed to the sliding block 213 of the sliding member 21 fixed on the second side 1312 of the supporting portion 131. The two fixed pulleys 35 can be rotatably attached to the two ends of the mounting portion 133, and one fixed pulley 35 can be located on the first side 1311 of the supporting portion 131 and the other fixed pulleys 35 can be located on the second side 1313 of the supporting portion 131. Referring to FIGS. 1 and 4, the connecting member 37 can be arranged on the two fixed pulleys 35, and one end of the connecting member 37 can be fixed to the mounting portion 311, and the other end of the connecting member 37 can be fixed to the lifting member 33. The weight elements 39 can be detachably fixed to the lifting member 33. The weight of the weight elements 39 can be selected according to the weight of electric screwdriver 400. When the electric screwdriver 400 are not located on the fixed portion 313, the gravity bear by one end of the connecting member 37 close to the lifting member 33 is greater than the gravity bear by the other end of the connecting member 37 close to the support member 31. When the electric screwdriver 400 are located on the fixed portion 313, the gravity bear by the end of the connecting member 37 close to the lifting member 33 is less that the gravity bear by the other end of the connecting member 37 close to the support member 31, and the support member 31 can slide along the sliding rail 211 towards the base plate 111. In this embodiment, the connecting member 37 can be wire rope.

The torsion measuring apparatus 300 can be located on the base plate 111, and further located between the two fixed plates 113. In detail, the torsion measuring apparatus 300 can include a measuring member 51 and a measuring connection 53 fixed on the measuring member 51. The measuring member 51 can be located on the base plate 111, and further located between the two fixed plates 113. The measuring connection 53 can be located on one side of the measuring member 51 away from the base plate 111, and further located below the fixed portion 311. The central axis of the measuring connection 53 can be aligned with the central axis of the holding portion 313.

Referring to FIGS. 2 and 3, the electric screwdriver 400 can include a resisting portion 60, the resisting portion 60 can include a second resisting surface 61 corresponding to the first resisting surface 3131.

Referring to FIGS. 1-4, when in assembly, the mounting member 13 can be fixed to the fixed member 11; the two sliding member 21 can be fixed to the first side 1311 and the second side 1312 of the supporting portion 131 respectively; the support member 31 and the lifting member 33 can be fixed to the corresponding sliding block 213 respectively; the two fixed pulleys 35 can be rotatably fixed to the two ends of the mounting portions 133; the connecting member 37 can be arranged on the two fixed pulleys 35; the two ends of the connecting member 37 can be connected to the fixed portion 311 of the support member 31 and the lifting member 33 respectively; the torsion test measuring device 300 can be fixed to the base plate 111, and the torsion test measuring device 300 can be located between the two fixed plates 113, and the electric screwdriver 300 can be located on the holding portion 313, and the second resisting surface 61 of the electric screwdriver 400 can be resisted on the first resisting surface 3131.

When in use, one end of the electric screwdriver 400 can pass through the taper hole 3130 of the holding portion 313 and the second through hole 3110 of the fixed portion 311, and the second resisting surface 61 of the electric screwdriver 400 can be resisted the first resisting surface 3131. When the electric screwdriver is located on the support member 31, the gravity bear by the end of the connecting member 37 close to the lifting member 33 is less that the gravity bear by the other end of the connecting member 37 close to the support member 31, and the support member 31 can slide along the sliding rail 211 towards the base plate 111 until the electric screwdriver 400 is engaged with the measuring connection 53. The motor (not shown) of the electric screwdriver 400 can drive the measuring connection 53 to rotate, and the measuring member 51 can measure the torsion value of the electric screwdriver 400.

In this embodiment, when the measuring member 51 measures the torsion value of the electric screwdriver 400, the force bear by the electric screwdriver 400 in the vertical direction can maintain its equilibrium, which increases the accuracy of the measurement of the electric screwdriver 400.

In at least one embodiment, the two sliding blocks 213 can be omitted, and the support member 31 and the lifting member 33 can be slidably attached to the corresponding sliding rail 211.

In at least one embodiment, the two fixed plates 113 can be omitted, and the supporting portion 131 can be fixed to the base plate 111 and further perpendicular to the base plate 111.

In at least one embodiment, the two fixed pulleys 35 can be fixed to the mounting portion 133 as long as the connecting member 37 can rotate relative to the two fixed pulleys 35.

In at least one embodiment, the four resisting members 25 can be omitted as long as the two ends of the sliding rail 211 have protrusions to prevent the support member 31 and the lifting member 33 sliding off the sliding rail 211.

In at least one embodiment, the holding portion 313 can be omitted as long as the electric screwdriver 400 can be located on the fixed portion 311.

The embodiments shown and described above are only examples. Many details are often found in the art. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure up to, and including the full extent established by the broad general meaning of the terms used in the claims. It will therefore be appreciated that the embodiments described above may be modified within the scope of the claims.

What is claimed is:

1. A supporting apparatus comprising:
 a supporting assembly comprising a fixed member and a mounting member fixed to the fixed member, the mounting member comprising a supporting portion having a first side, a second side opposite and parallel to the first side, and a top side coupling the first side with the second side; and
 a lifting assembly comprising:
  a support member slidably attached to the first side of the supporting portion, wherein the support member defines a first through hole away from the supporting portion, a central axis of the first through hole is in a vertical direction, the first through hole comprises a taper hole and a second through hole, and a central axis of the second through hole is aligned with a central axis of the taper hole;
  a lifting member slidably attached to the second side of the supporting portion;
  a connecting member coupling the support member with the lifting member; and
  one or more weight elements attachable to the lifting member.

2. The supporting apparatus of claim 1, wherein the support member comprises a fixed portion and a holding portion fixed to the fixed portion, the fixed portion is fixed to the first side of the supporting portion, and further define the second through hole away from the supporting portion, the holding portion has a first resisting surface, and the taper hole is formed by the first resisting surface.

3. The supporting apparatus of claim 2, wherein a diameter of the taper hole close to the fixed portion is less than a diameter of the taper hole away from the fixed portion.

4. The supporting apparatus of claim 1, wherein the lifting assembly further comprises at least one fixed pulley attached to the top side of the supporting portion, the connecting member arranged on the at least one fixed pulley.

5. The supporting apparatus of claim 4, wherein the mounting member comprises a mounting portion fixed to the supporting portion distal from the fixed member, the at least one fixed pulleys are two fixed pulleys, the two fixed pulleys are rotatably fixed to the supporting portion, and one fixed pulley is located on the first side of the supporting portion, and the other fixed pulleys is located on the second side of the supporting portion.

6. The supporting apparatus of claim 1, wherein the supporting apparatus further comprises a sliding assembly, the sliding assembly comprises two sliding member, each sliding member comprises a sliding rail, one sliding rail is fixed to the first side of the supporting portion, and the other sliding rail is fixed to the second side of the supporting portion, the support member is slidably attached to the one sliding rail, and the lifting member is slidably attached to the other sliding rail.

7. The supporting apparatus of claim 6, wherein each sliding member comprises a sliding block slidably attached to the sliding rail, the support member and the lifting member are fixed to the two sliding blocks respectively.

8. The supporting apparatus of claim 6, wherein the sliding assembly further comprises four resisting members, two of the four resisting members are located on the sliding rail fixed to first side of the supporting portion, and the other two of four resisting members are located on the other sliding rail fixed to the second side of the supporting portion.

9. A torsion test measuring device, comprising:
 an electric screwdriver;
 a torsion measuring apparatus; and
 a supporting apparatus, wherein the supporting apparatus comprises
  a supporting assembly comprising a fixed member and a mounting member fixed to the fixed member, the mounting member comprising a supporting portion having a first side, a second side opposite and parallel to the first side, and a top side coupling the first side with the second side; and
  a lifting assembly comprising:
   a support member slidably attached to the first side of the supporting portion;
   a lifting member slidably attached to the second side of the supporting portion;
   at least one fixed pulley attached to the top side of the supporting portion;
   a connecting member arranged on the at least one fixed pulley, and coupling the support member with the lifting member; and
   one or more weight elements attachable to the lifting member;
  wherein the torsion measuring apparatus is located on the fixed member, and the electric screwdriver is located on the support member.

10. The torsion test measuring device of claim 9, wherein the support member defines a first through hole away from the mounting portion, a central axis of the first through hole is in a vertical direction, the first through hole comprises a taper hole and a second through hole, and a central axis of the second through hole is aligned with a central axis of the taper hole, the electric screwdriver is located in the first through hole, a central axis of the electric screwdriver is aligned with the central axis of the first through hole, and the electric screwdriver resists the taper hole.

11. The torsion test measuring device of claim 10, wherein the support member comprises a fixed portion and a holding portion fixed to the fixed portion, the fixed portion is fixed to the first side of the supporting portion, and further define the second through hole away from the supporting portion, the holding portion has a first resisting surface, and the taper hole is formed by the first resisting surface, the electric screwdriver comprises a resisting portion, the resisting portion comprises a second resisting surface, the second resisting surface is resisted the first resisting surface.

12. A torsion test measuring device comprising:
 a torsion measuring apparatus with a measuring connection selectively engagable with a to-be-tested device;
 a supporting apparatus having:
  a fixed member; and
  a mounting member attached on the fixed member, the mounting member being substantially perpendicular to the fixed member, the mounting member comprising a supporting portion, the supporting portion having a first side, a second side, opposite, and substantially parallel, to the first side, and a top side connecting the first side to the second side, the top side being substantially perpendicular to the first side and the second side and positioned furthest from the fixed member; and
 a lifting assembly having:
  a support member slidably attached to the first side;
  a lifting member slidably attached to the second side;
  a connecting member coupling the support member to the lifting member; and
  one or more weight elements attachable to the lifting member;
 wherein, the torsion measuring apparatus in positioned on the fixed member; and wherein, the to-be-tested device is positionable upon the support member and slidably engagable with the measuring connection when the support member moves along the first side, towards the fixed member, and the lifting member moves along the second side, towards the top side, wherein the support member defines a first through hole away from the supporting portion, a central axis of the first through hole is in a vertical direction, the first through hole comprises a taper hole and a second through hole, and a central axis of the second through hole is aligned with a central axis of the taper hole, the electric screwdriver is located in the first through hole, a central axis of the electric screwdriver is aligned with the central axis of the first through hole, and the electric screwdriver resists the taper hole.

13. The torsion test measuring device of claim 12, wherein the lifting assembly further comprises at least one fixed pulley attached to the top side of the supporting portion, the connecting member arranged on the at least one fixed pulley.

14. The torsion test measuring device of claim 12, wherein the support member comprises a fixed portion and a holding portion fixed to the fixed portion, the fixed portion is fixed to the first side of the supporting portion, and further define a second through hole away from the supporting portion, the holding portion has a first resisting surface, and the taper hole is formed by the first resisting surface, the electric screwdriver comprises a resisting portion, the resisting portion comprises a second resisting surface, the second resisting surface is resisted the first resisting surface.

* * * * *